United States Patent [19]

Rogalsky et al.

[11] Patent Number: 5,425,720
[45] Date of Patent: Jun. 20, 1995

[54] MEDICAL NEEDLE UNIT

[76] Inventors: Alena Rogalsky; Vitaly Rogalsky, both of 186 Pinehurst Ave., New York, N.Y. 10036

[21] Appl. No.: 9,983
[22] Filed: Jan. 27, 1993
[51] Int. Cl.6 .............................................. A61M 5/32
[52] U.S. Cl. ..................................... 604/198; 604/192
[58] Field of Search ........................ 604/192, 198, 263

[56] References Cited

U.S. PATENT DOCUMENTS

| | | | |
|---|---|---|---|
| 4,139,009 | 2/1979 | Alvarez | 604/198 |
| 4,804,371 | 2/1989 | Vaillancourt | 604/198 |
| 4,892,521 | 1/1990 | Laico et al. | 604/198 |
| 4,911,706 | 3/1990 | Levitt | 604/198 |
| 4,955,866 | 9/1990 | Corey | 604/198 |
| 5,059,180 | 10/1991 | McLees | 604/198 |
| 5,120,321 | 6/1992 | Oksman et al. | 604/263 |
| 5,183,468 | 2/1993 | McLees | 604/198 |

Primary Examiner—John G. Weiss
Attorney, Agent, or Firm—I. Zborovsky

[57] ABSTRACT

A medical needle unit has a front end with a tip and a rear end and insertable with a tip in as well as withdrawal from the body of a patient, a protective element for preventing accidental puncture by the tip of the needle after the withdrawal of the needle from the body, the protective element including a hood movable between an exposing position in which the tip of the needle is exposed and an enclosed position in which the tip of the needle is enclosed, a spring connecting with the hood so that when the spring is compressed the hood is in the exposed position and when the spring is relaxed the hood is in the enclosed position, and a retaining element which retain the spring in the compressed position and therefore the hood in the exposing position before an injection by the needle and is releasable during the injection so as to relax the spring and to move the hood to the enclosing position.

6 Claims, 4 Drawing Sheets

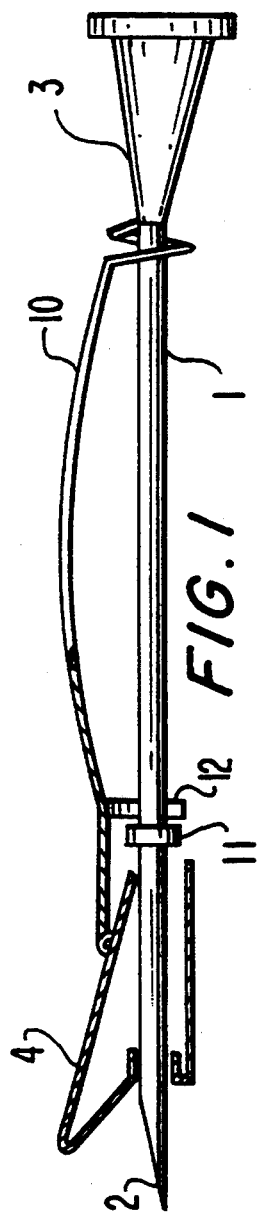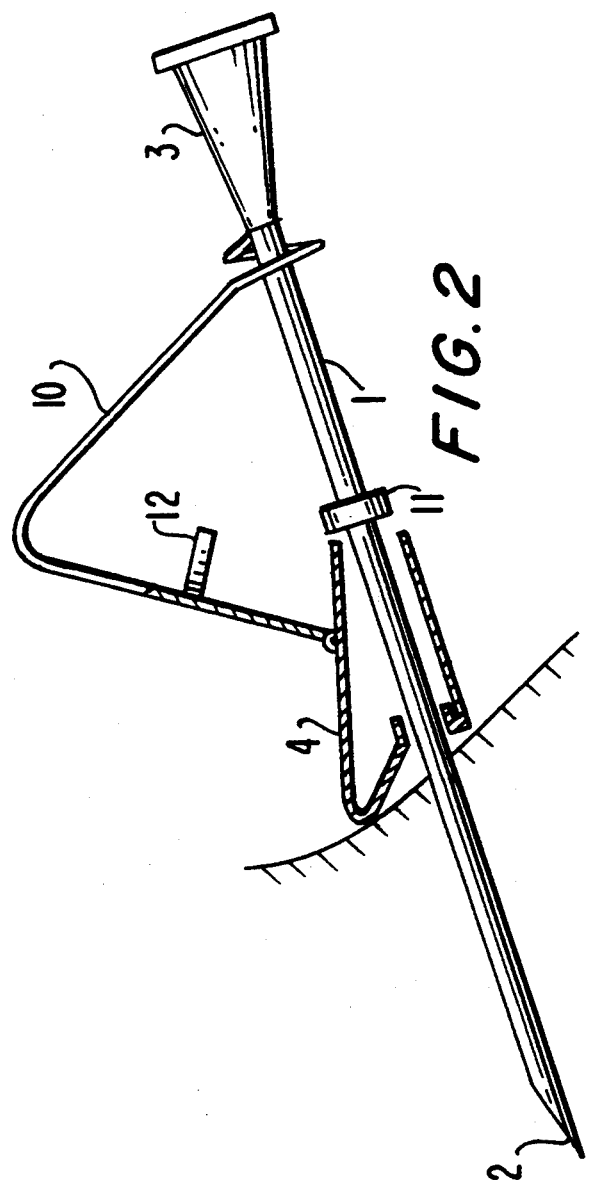

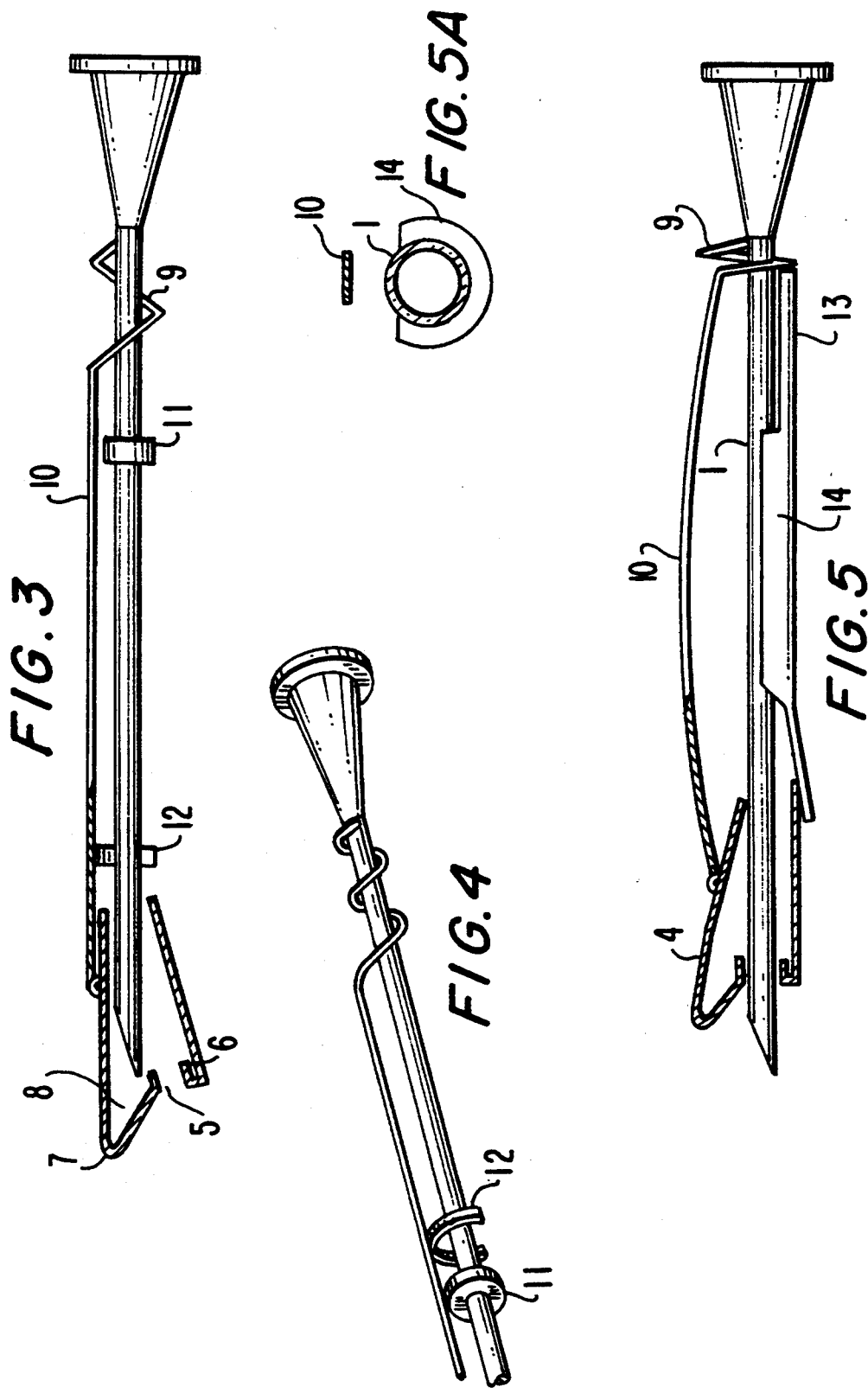

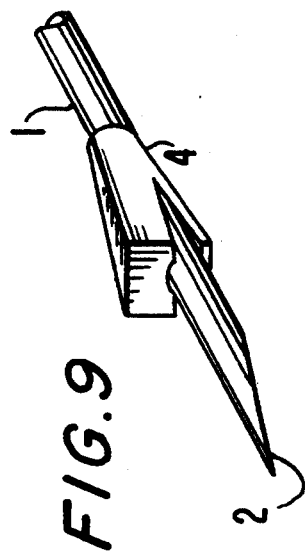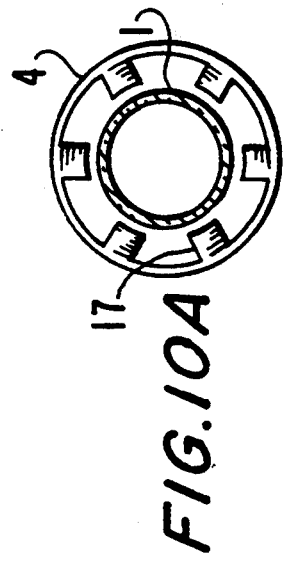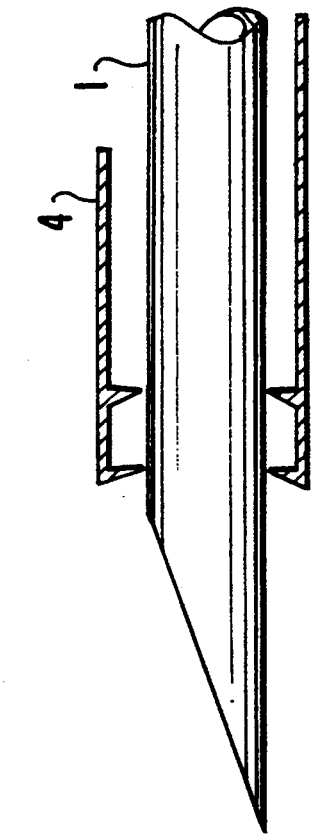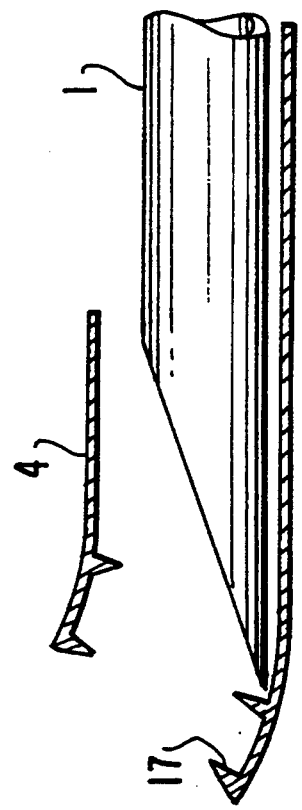
FIG. 9
FIG. 10A
FIG. 10
FIG. 11

MEDICAL NEEDLE UNIT

BACKGROUND OF THE INVENTION

The present invention relates to medical needle units.

Medical needle units are widely known and used for injection and withdrawal of blood or other tissue fluids. After the withdrawal of blood or other tissue fluids, the needle of the needle unit is withdrawn from a muscle, vein, artery or another body area and a tip of the needle is exposed. The needle may contaminated with microorganisms, and it is possible that a technician, nurse or physician can be accidentally punctured by the exposed needle tip. In the event of contamination of the needle with viruses, etc. it can lead to very serious or even grave consequences. It is to be understood that it is desirable or at least decrease the tendency of the operator to be accidentally struck by an exposed needle tip.

Several solutions have been proposed to avoid the accidental puncture. One of such solutions includes for example a cylindrical hood which is movably attached to the needle which moves first to an exposing position in which the tip of the needle is exposed before the injection and back to enclosing position in which the cylindrical hood encloses the tip of the needle after the injection. Another solution is a hood which moves along the syringe and is also displaced to cover the needle. It is believed that the existing solutions are quite complicated, not self-operating, need additional procedures. It is therefore desirable to develop further protective elements for medical needle units which are simpler, less expensive, reliable and self-operation.

SUMMARY OF THE INVENTION

Accordingly, it is an object of the present invention to provide a medical needle unit which includes a needle and a protective element, which is a dramatic improvement of the existing protecting elements.

In keeping with these objects and with others which will become apparent hereinafter, one feature of the present invention resides, briefly stated, in a medical needle unit which has a front end with a tip and a rear end and insertable with a tip in as well as withdrawal from the body of a patient, a protective element for preventing accidental puncture by the tip of the needle after the withdrawal of the needle from the body, the protective element including a hood movable between an exposing position in which the tip of the needle is exposed and an enclosed position in which the tip of the needle is enclosed, a spring connecting with the hood so that when the spring is compressed the hood is in the exposed position and when the spring is relaxed the hood is in the enclosed position, and a retaining element which retain the spring in the compressed position and therefore the hood in the exposing position before an injection by the needle and is releasable during the injection so as to relax the spring and to move the hood to the enclosing position.

When the medical needle units is designed in accordance with the present invention, it avoids the disadvantages of the prior art and provides for a simple, self-operating and reliable protection from accidental punctures by a needle tip.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

FIGS. 1-3 are view showing a first embodiment of a medical needle unit with a protective element before injection, during the injection and after the injection correspondingly;

FIG. 4 is a view showing a further modification of a spring element of the inventive medical needle unit;

FIGS. 5 and 6 are views showing two further modifications of the protective elements of the inventive medical needle unit;

FIG. 5a is an end view of the protective element of FIG. 5.

FIG. 9 is a view of the unit formed as a jaw; and

FIGS. 10, 10a and 11 are views showing a further modification of the inventive protective element.

DESCRIPTION OF THE PREFERRED EMBODIMENTS

Figure 6:
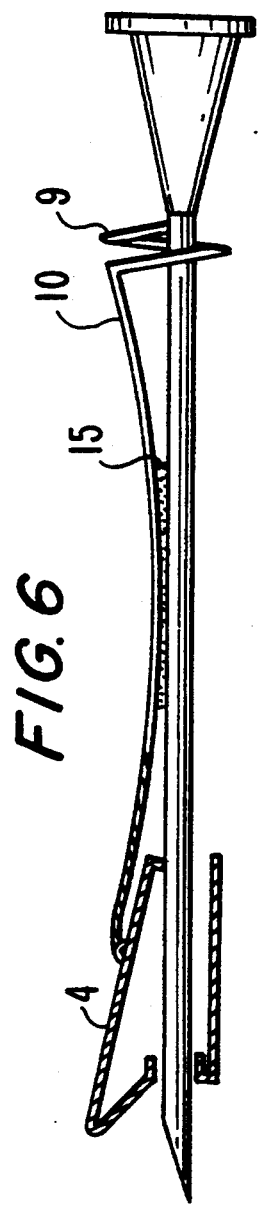

A medical needle unit in accordance with the present invention has a medical needle which is identified as a whole with reference numeral 1 and has a tip 2 and a rear end 3. The unit further has a short hood which is identified with reference numeral 4. The hood 4 has a conical shape and is provided with a front passage 5 formed by two parallel strips 6 extending rearwardly from the front surface 7 of the hood and forming two pockets 8 at opposite sides of the passage 5. The unit further has a spring 9 which is arranged on the rear end 3 of the needle 1 and connected with the hood 4 by a connecting element 10. The connecting element 10 can be also formed of a springy material.

The unit in accordance with the embodiment of FIGS. 1-3 has also retaining means which includes a stop member 11 fixedly arranged on the needle 1 and a projection 12 arranged on the connecting element 10. The projection 12 may be formed as a U-shaped with two legs embracing the needle 1.

The medical needle unit in accordance with the embodiment of FIGS. 1-3 operates in the following manner: Before the injection in the position shown in FIG. 1, the projection 12 is located behind the stop 11, the spring 9 is compressed, and the hood 4 is withdrawn so that the tip 2 of the needle 1 is exposed. During the injection, as shown in FIG. 2, the hood 2 is further moved rearwardly along the needle 1, the projection 12 is lifted perpendicularly to the needle 1 and jumps over the stop 11 so as to be located forwardly of the stop 11. When the needle is withdrawn from the body of a patient the spring 9 is relaxed and the hood 4 moves forward under the action of the spring, so that the tip of the needle 2 is located in the upper pocket 8 of the hood 4. Therefore, the tip is completely enclosed, and there is no danger of puncturing of personnel by the needle.

In the embodiment of FIGS. 1-3 the spring 9 is formed with flat convolutions. However, it is of course possible to form the spring 9 as a purely helical spring as shown in FIG. 4.

In the embodiment of FIG. 5, the retaining means is formed in a somewhat different manner. The retaining means includes an element 13 which has a portion 14 of a semi-circular cross-section, as shown in FIG. 5a. The element 13 together with the portion 14 have a springy action, and therefore the semi-circular portion 14 is firmly retained on the needle 1 by its springy action on the needle 1 before the injection so that the spring 9 is compressed. During the injection the hood 4 is moved rearwardly and its rear end moves underneath the element 13 and removes it from the needle 1. After the injection, since the element 13 is removed from the needle, the spring 9 relaxes and pushes the hood 4 through the element 10 to the enclosing position, corresponding to the position of FIG. 3 so that the tip of the needle is reliably enclosed in the pocket of the hood.

In the embodiment of FIG. 6 the retaining means is a layer of glue 15 which adhesively connects the connecting element with the needle 1 and holds the spring 9 in its compressed position before the injection. During the injection the hood 4 is displaced rearwardly and its rear end removes the layer of glue 15 and releases the element 10 and therefore the spring. After the injection, the spring 9 pushes the element 10 forwardly and therefore the hood 4 forwardly as well, and the hood 4 assumes its enclosing position.

The hood 4 is composed of an elastic material, so that it can slide over the needle, and its closing portions lose-when-the hood is displaced beyond the needle after the injection and extend into one another. The inclined edge of the semi-circular portion 14 of the element 13 provides for an easy separation of-the element 13 during the operation. Other structural features are self-explanatory.

Figure 8:
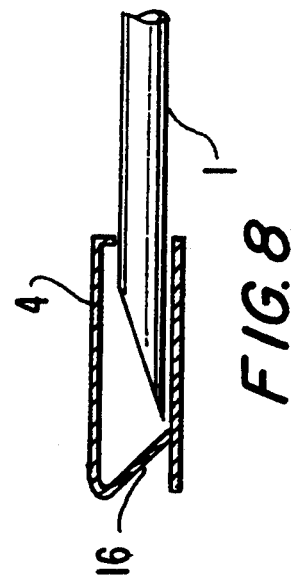
FIGS. 7 and 8 are views showing a further modification of the unit before and after injection.
Figure 7:
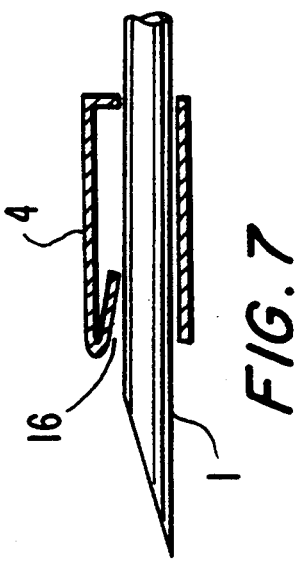

In the embodiment of FIGS. 7 and 8 the hood is provided with a front strip 16 which is bent inwardly, into the interior of the hood. In the extended position of the needle the strip rests on its outer surface. When the needle retracts back, the strip closes the outlet opening of the hood and therefore provide for a reliable injury prevention for the operator.

In the embodiment of FIG. 9 the hood is formed as a jaw, in a simple and reliable way.

In the embodiment of FIG. 10-10A-11 the hood is formed of resilient tubing with 17 interior protrusions, and which curves when the needle retracts back and covers the tip.

The invention is not limited to the details shown since various modifications and structural changes are possible without departing in any way from the spirit of the invention.

What is desired to be protected by Letters Patent is set forth in the appended claims.

We claim:

1. A medical needle unit, comprising a needle having a tip insertable in as well as withdrawable from the body of a patient; a protective element for preventing accidental puncture by said tip of said needle after the withdrawal of said tip of said needle from the body, said protective element including a hood movable between an exposing position in which said tip of said needle is exposed and an enclosing position in which said tip of said needle is enclosed, a spring connected with said hood so that when the spring is compressed said hood is in said exposed position and when said spring is relaxed said hood is in said enclosing position, and a retaining element which retains said spring in said compressed position and therefore said hood in said exposing position before an injection by said needle, said retaining element is displaceable during the injection so as to relax said spring and to move said hood to said enclosing position; a connecting element which connects said hood with said spring and extends substantially along said needle, said retaining element being formed as a glue layer which fixes said connecting element to said needle in said compressed position of said spring, and during the injection is removed by said hood so as to allow the relaxation of said spring.

2. A medical needle unit as defined in claim 1, wherein said connecting element is formed as a springy element.

3. A medical needle unit as defined in claim 1, wherein said spring has with straight windings.

4. A medical needle unit as defined in claim 1, wherein said spring has helical windings.

5. A medical needle unit, comprising a needle having a tip insertable in as well as withdrawable from the body of a patient; a protective element for preventing accidental puncture by said tip of said needle after the withdrawal of said tip of said needle from the body, said protective element including a hood movable between an exposing position in which said tip of said needle is exposed and an enclosing position in which said tip of said needle is enclosed, a spring connected with said hood so that when the spring is compressed said hood is in said exposed position and when said spring is relaxed said hood is in said enclosing position, and a retaining element which retains said spring in said compressed position and therefore said hood in said exposing position before an injection by said needle, said retaining element is displaceable during the injection so as to relax said spring and to move said hood to said enclosing position; a connecting element which connects said hood with said spring and extends substantially along said needle, said retaining element including a stop member arranged on said needle and an engaging member arranged in said connecting element and located behind said stop member in said compressed position of said spring, said engaging element during injection moving first perpendicularly to said needle and then jumping over said stop member so as to move forward of said stop member after the injection.

6. A medical needle unit, comprising a needle having a tip insertable in as well as withdrawable from the body of a patient; a protective element for preventing accidental puncture by said tip of said needle after the withdrawal of said tip of said needle from the body, said protective element including a hood movable between an exposing position in which said tip of said needle is exposed and an enclosing position in which said tip of said needle is enclosed, a spring connected with said hood so that when the spring is compressed said hood is in said exposed position and when said spring is relaxed said hood is in said enclosing position, and a retaining element which retains said spring in said compressed position and therefore said hood in said exposing position before an injection by said needle, said retaining element is displaceable during the injection so as to relax said spring and to move said hood to said enclosing position; a connecting element which connects said hood with said spring and extends substantially along said needle, said retaining element including a substantially semicircularly springy member which is clamped on said needle by its springy action in said compressed position of said spring and during the injection is removed from said needle by said hood to allow the relaxation of said spring.

* * * * *